United States Patent
Metcalf

(10) Patent No.: US 10,555,914 B1
(45) Date of Patent: Feb. 11, 2020

(54) METHODS OF PRODUCING ANIONIC CANNABINOID MOLECULES DISSOLVED IN WATER

(71) Applicant: Natural Extraction Systems, LLC, Boulder, CO (US)

(72) Inventor: Douglas G. Metcalf, Erie, CO (US)

(73) Assignee: Natural Extraction Systems, LLC, Boulder, CO (US)

( * ) Notice: Subject to any disclaimer, the term of this patent is extended or adjusted under 35 U.S.C. 154(b) by 0 days.

(21) Appl. No.: 16/440,878

(22) Filed: Jun. 13, 2019

Related U.S. Application Data

(60) Provisional application No. 62/780,176, filed on Dec. 14, 2018, provisional application No. 62/787,720, filed on Jan. 2, 2019, provisional application No. 62/812,845, filed on Mar. 1, 2019.

(51) Int. Cl.
*A61K 31/05* (2006.01)
*A61K 9/00* (2006.01)

(52) U.S. Cl.
CPC ............ *A61K 31/05* (2013.01); *A61K 9/0095* (2013.01)

(58) Field of Classification Search
CPC ..................................................... A61K 31/05
See application file for complete search history.

(56) References Cited

U.S. PATENT DOCUMENTS

2019/0030170 A1\* 1/2019 Kingsley ................ A61K 47/40

\* cited by examiner

*Primary Examiner* — Adam C Milligan
*Assistant Examiner* — Sarah Alawadi
(74) *Attorney, Agent, or Firm* — Cooley LLP

(57) ABSTRACT

Various aspects of this patent document relate to methods to produce compositions comprising anionic cannabinoid molecules.

16 Claims, 1 Drawing Sheet

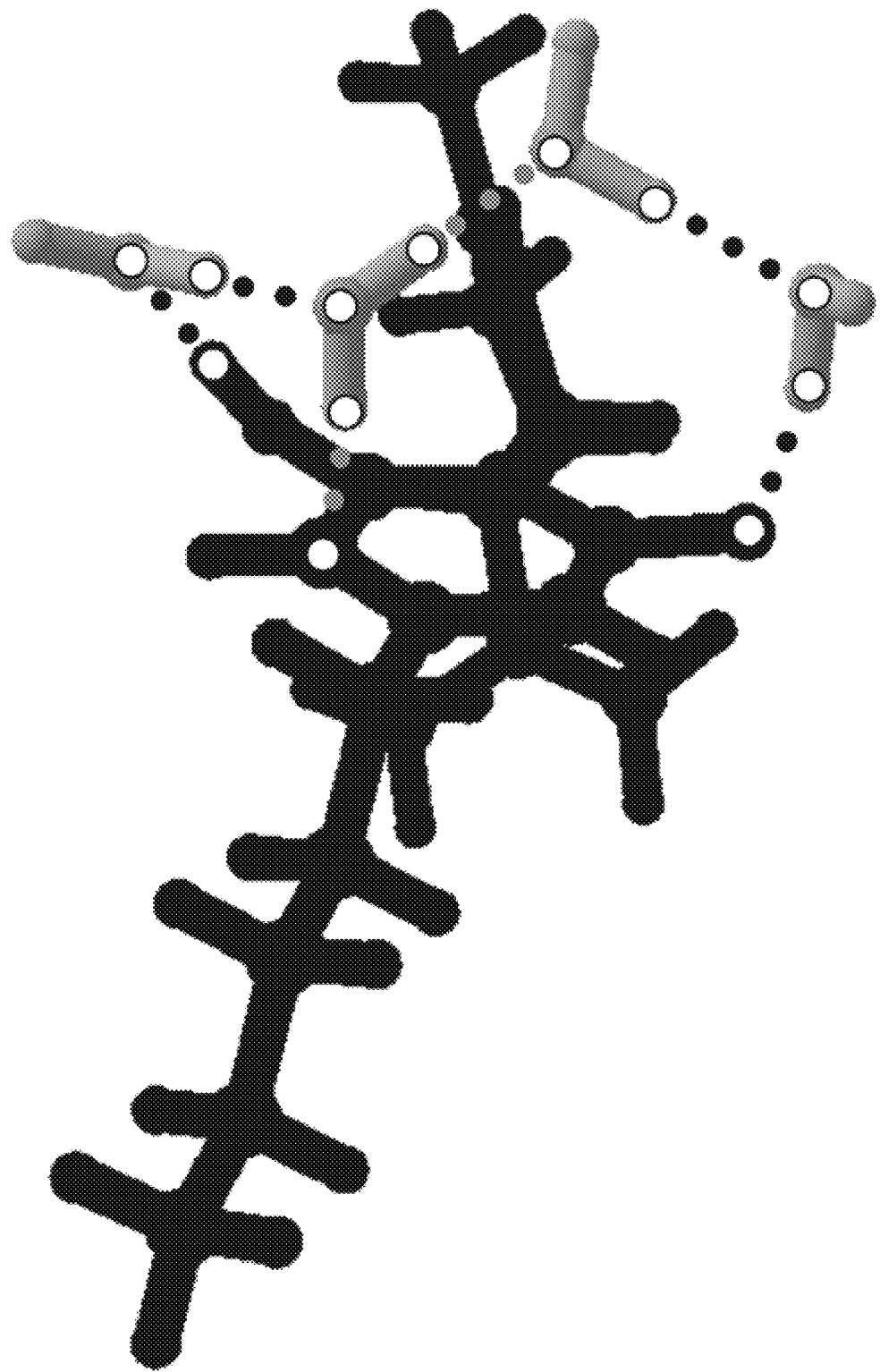

METHODS OF PRODUCING ANIONIC CANNABINOID MOLECULES DISSOLVED IN WATER

CROSS-REFERENCE TO RELATED APPLICATIONS

This patent document claims priority to U.S. Provisional Patent Application No. 62/780,176, filed Dec. 14, 2018, U.S. Provisional Patent Application No. 62/787,720, filed Jan. 2, 2019, and U.S. Provisional Patent Application No. 62/812,845, filed Mar. 1, 2019, each of which is incorporated by reference in its entirety.

BACKGROUND

Cannabinoids that lack a carboxyl group are insoluble in water. Attempts have been made to suspend cannabinoids in water to produce beverages, for example, by emulsification. Stable emulsions frequently display unfavorable characteristics such as undesirable flavor and poor bioavailability. Methods to dissolve cannabinoids in water could disrupt the beverage industry.

SUMMARY

Various aspects of this patent document relate to anionic cannabinoid molecules. Specific aspects of this patent document relate to methods to produce compositions comprising anionic cannabinoid molecules.

BRIEF DESCRIPTION OF THE DRAWINGS

The FIGURE is a two-dimensional rendering of a three-dimensional model of 2-[(1R,6R)-6-isopropenyl-3-methylcyclohex-2-en-1-yl]-3-hydroxy-5-pentylphenolate (black) bound to four water molecules (grey). Six hydrogen bonds are depicted with dotted lines.

DETAILED DESCRIPTION

Various aspects of this patent document relate to the discovery that anionic cannabinoid molecules are water-soluble at mildly-alkaline pH. This discovery was surprising and unexpected because previously-reported $pK_a$ values of various cannabinoids were relatively high. The $pK_a$ of cannabidiol has been reported as ranging from 9.13 to 9.64, for example, and the $pK_a$ of tetrahydrocannabinol has been reported as 10.6. The present disclosure reveals that the $pK_a$'s of cannabinoids dissolved in dilute aqueous solution are lower than previously-reported values.

The term "anionic cannabinoid molecule" refers to a cannabinoid molecule that carries a net negative charge. Anionic cannabinoid molecules include, but are not limited to, cannabinoid molecules that have a deprotonated hydroxyl oxygen such that either (i) the molecule contains an oxide, such as a phenolate, or (ii) a resonance structure of the molecule contains an oxide, such as a phenolate. In some specific embodiments, an anionic cannabinoid molecule is not a carboxylate. In some very specific embodiments, an anionic cannabinoid molecule lacks a carboxyl or carboxylate.

To determine the $pK_a$'s of cannabinoids in water, cannabinoids were dissolved in water, which was technically challenging as described in the exemplification section and has never been previously reported. Many unsuccessful solubilization methods were attempted, some of which are described in the exemplification section, and broadly-applicable methods that yield consistent results were eventually developed. Cannabinoids dissolve in water, for example, after first deprotonating a cannabinoid with a strong Brønsted base in ethanol and then diluting the ethanol with water comprising another Brønsted base. The discovery of lower-than-expected $pK_a$ values for cannabinoids dissolved in water allowed the development of beverages containing anionic cannabinoid molecules, which have surprisingly advantageous properties never-before encountered in any consumer product.

Beverages containing anionic cannabinoid molecules have an intense color at commercially-relevant concentrations, which allows consumers to verify the identity and approximate concentration of an anionic cannabinoid molecule in a product with the unaided eye. The intense color rapidly dissipates upon contacting an anionic cannabinoid molecule with a weak acid such as the carbonic acid of carbonated water or the citric acid of a *Citrus* fruit, which allows consumers to readily authenticate that a color corresponds to an anionic cannabinoid molecule rather than an adulterant without any analytical devices or reagents. These features are especially useful in the nutritional supplement industry, for example, because many finished-product manufacturers allow varying precision and accuracy in the content of their active ingredients. Variable precision or accuracy results in variable efficacy. Unsophisticated manufacturers and unscrupulous manufacturers similarly formulate beverages with cannabidiol isolate particles that lack any bioavailability because humans cannot dissolve, melt, or otherwise digest cannabidiol isolate. The color and color change allow novel marketing by showcasing methods to validate a product, which could provide consumer confidence that transcends brand recognition.

Anionic cannabinoid molecules rapidly reprotonate upon ingestion, which causes them to adhere to the gastrointestinal lining and favors absorption in the mouth, esophagus, and stomach. Historical ingestible cannabinoid formulations favor absorption in the small intestine, which provides significantly slower onset. The effective accessible surface area of an anionic cannabinoid molecule formulation is also orders-of-magnitude greater than the effective accessible surface area of historical cannabinoid formulations because dissolved anionic cannabinoids are not sequestered by lipids, surfactants, or emulsifiers. Increased surface area further increases absorption rates. These unique pharmacokinetic properties allow rapid onset and acute pharmacological effects that have never been previously reported for orally-administered cannabinoids.

The conjugate base of cannabidiol dissolved in water displays rapid, psychoactive effects less than 5 minutes after ingestion, which is extraordinarily rapid for an orally-administered compound. The rapid onset of pharmacological activity suggests that anionic cannabinoid molecules are absorbed in the mouth, and possibly through the epithelial lining of the esophagus. Additionally, cannabidiol is not known to display a notable psychoactive effect. The rapid absorption of the conjugate base of cannabidiol in the mouth likely results in an abrupt bolus of cannabidiol in the blood, which was not previously feasible. Cannabidiol may be marginally psychoactive, and the oral administration of the conjugate base of cannabidiol might allow the marked perception of this psychoactive effect.

Various aspects of this patent document relate to a composition.

Various aspects of this patent document relate to a container comprising a sealed chamber, in which the container contains a composition in the sealed chamber.

In some embodiments, a composition comprises water and an anionic cannabinoid molecule, in which the anionic cannabinoid molecule is dissolved in the water.

The term "dissolved" refers to a molecule that is a solute of a solvent such as water. A molecule that is merely suspended within a solvent, such as a molecule of an emulsion, is not dissolved. A cannabinoid molecule that is non-covalently associated with another cannabinoid molecule, another lipid, or an amphiphilic molecule within water is not dissolved in the water.

In some embodiments, an anionic cannabinoid molecule is 2-[6-isopropenyl-3-methylcyclohex-2-en-1-yl]-3-hydroxy-5-pentylphenolate. In some specific embodiments, an anionic cannabinoid molecule is 2-[1R,6R)-6-isopropenyl-3-methylcyclohex-2-en-1-yl]-3-hydroxy-5-pentylphenolate.

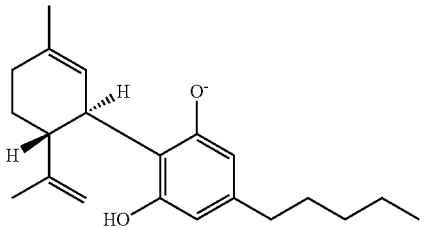 [SMILES: C=C(C)[C@@H]1CCC(C)=C[C@H]1c1c([O-])cc(CCCCC)cc1O]

2-[(1R,6R)-6-isopropenyl-3-methylcyclohex-2-en-1-yl]-3-hydroxy-5-pentylphenolate In some embodiments, a composition comprises 2-[(1R,6R)-6-isopropenyl-3-methylcyclohex-2-en-1-yl]-3-hydroxy-5-pentylphenolate and 2-[(1R,6R)-6-isopropenyl-3-methylcyclohex-2-en-1-yl]-5-pentylbenzene-1,3-diol at a molar ratio of 1:10 to 10,000:1. In some specific embodiments, a composition comprises 2-[(1R,6R)-6-isopropenyl-3-methylcyclohex-2-en-1-yl]-3-hydroxy-5-pentylphenolate and 2-[(1R,6R)-6-isopropenyl-3-methylcyclohex-2-en-1-yl]-5-pentylbenzene-1,3-diol at a molar ratio of 1:1 to 10,000:1. In some very specific embodiments, a composition comprises 2-[(1R,6R)-6-isopropenyl-3-methylcyclohex-2-en-1-yl]-3-hydroxy-5-pentylphenolate and 2-[(1R,6R)-6-isopropenyl-3-methylcyclohex-2-en-1-yl]-5-pentylbenzene-1,3-diol at a molar ratio of 2:1 to 10,000:1.

In some embodiments, a composition comprises water and a plurality of anionic cannabinoid molecules, and each anionic cannabinoid molecule of the plurality of anionic cannabinoid molecules is dissolved in the water.

In some embodiments, a plurality of anionic cannabinoid molecules comprises 2-[(1R,6R)-6-isopropenyl-3-methylcyclohex-2-en-1-yl]-3-hydroxy-5-pentylphenolate and one or more anionic cannabinoid molecules selected from 2-[(1R,6R)-6-isopropenyl-3-methylcyclohex -2-en-1-yl]-3-hydroxy-5-propylphenolate; 2-[(1R,6R)-6-isopropenyl-3-methylcyclohex -3-en-1-yl]-3-hydroxy-5-pentylphenolate; 2-[(1R,6R)-6-isopropenyl-3-methylcyclohex-3-en-1-yl]-3-hydroxy-5-propylphenolate; 2-[(1R,6R)-6-isopropenyl-3-methylcyclohex-2-en-1-yl]-5-pentyl-1,4-benzoquinone-3-oxide; 3-[(1R,6R)-6-isopropenyl-3-methylcyclohex-2-en-1-yl]-6-pentyl-1,2-benzoquinone-4-oxide; 2-[(1R,6R)-6-isopropenyl-3-methylcyclohex-3-en-1-yl]-5-pentyl-1,4-benzoquinone-3-oxide; 3-[(1R,6R)-6-isopropenyl-3-methylcyclohex-3-en-1-yl]-6-pentyl-1,2-benzoquinone-4-oxide; 2-[(1R,6R)-6-isopropenyl-3-methylcyclohex-2-en-1-yl]-5-propyl-1,4-benzoquinone-3-oxide; 3-[(1R,6R)-6-isopropenyl-3-methylcyclohex-2-en-1-yl]-6-propyl-1,2-benzoquinone-4-oxide; 2-[(1R,6R)-6-isopropenyl-3-methylcyclohex-3-en-1-yl]-5-propyl-1,4-benzoquinone-3-oxide; 3-[(1R,6R)-6-isopropenyl-3-methylcyclohex-3-en-1-yl]-6-propyl-1,2-benzoquinone-4-oxide; (6aR,10aR)-6,6,9-trimethyl-3-pentyl-6a,7,8,10a-tetrahydro-6H-benzo[c]chromen-1-oxide; (6aR,10aR)-6,6,9-trimethyl-3-propyl-6a,7,8,10a-tetrahydro-6H-benzo[c]chromen-1-oxide; (6aR,10aR)-6,6,9-trimethyl-3-pentyl-6a,7,10,10a-tetrahydro-6H-benzo[c]chromen-1-oxide; (6aR,10aR)-6,6,9-trimethyl-3-propyl-6a,7,10,10a-tetrahydro-6H-benzo[c]chromen-1-oxide; 2-[(2E)-3,7-dimethylocta-2,6-dienyl]-3-hydroxy-5-pentylphenolate; and 2-[(2E)-3,7-dimethylocta-2,6-dienyl]-3-hydroxy-5-propylphenolate.

In some embodiments, a composition comprises an anionic cannabinoid molecule, and the anionic cannabinoid molecule is associated with one or more counterions in the composition. In some specific embodiments, a composition comprises an anionic cannabinoid molecule and one or more counterions selected from potassium ion, sodium ion, magnesium ion, and calcium ion.

In some embodiments, a composition has a color, and the color is purple. A composition that has a purple color preferentially absorbs yellow frequencies of light and preferentially transmits violet frequencies of light such that a human observer observes that the composition is a shade of purple.

In some embodiments, a container contains a composition; the container is physically associated with a label; and the label comprises an image of a reference color. In some specific embodiments, a container contains a composition; the container is physically associated with a label; and the label comprises an image of a reference color to provide a consumer or other individual with a reference to an intended or desired color of the composition. In some very specific embodiments, a container contains a composition; the container is physically associated with a label; the label comprises an image of a reference color to provide a consumer or other individual with a reference to an intended or desired color of the composition; and the reference color is purple. In some very specific embodiments, a container contains a composition; the container is physically associated with a label; the composition has an actual color; the label comprises an image of a reference color to provide a consumer or other individual with a reference to an intended or desired color of the composition; and the actual color corresponds to the reference color.

The term "corresponds" refers to approximate identity as perceived by an average, unaided human eye such that (i) an actual color corresponds to a reference color if the actual color and the reference color are approximately the same as perceived by an average, unaided human eye (for example, an unaided human eye may perceive that an actual color and a reference color are both either red, orange, yellow, green, blue, or purple), (ii) an actual shade corresponds to a reference shade if the actual shade and the reference shade are approximately the same as perceived by an average, unaided human eye (for example, an unaided human eye may perceive that an actual shade of purple and a reference shade of purple are both either indigo or violet), and (iii) an actual intensity corresponds to a reference intensity if the actual intensity and the reference intensity are approximately the same as perceived by an average, unaided human eye.

In some embodiments, a container contains a composition; the composition has an actual color; the actual color has an actual shade; a label is attached to the container; the label comprises an image of a reference color to provide a consumer or other individual with a reference to an intended or desired color of the composition; the reference color has a reference shade; the actual color corresponds to the reference color; and the actual shade corresponds to the reference shade. In some specific embodiments, a container contains a composition; the composition has an actual color; the actual color is purple; the actual color has an actual shade; the actual shade is a shade of purple; a label is attached to the container; the label comprises an image of a reference color to provide a consumer or other individual with a reference to an intended or desired color of the composition; the reference color is purple; the reference color has a reference shade; and the reference shade is the shade of purple. In some very specific embodiments, a container contains a composition; the composition has an actual color; the actual color has an actual shade and an actual intensity; a label is attached to the container; the label comprises an image of a reference color to provide a consumer or other individual with a reference to an intended or desired color of the composition; the actual color corresponds to the reference color; the reference color has a reference shade and a reference intensity; the actual shade corresponds to the reference shade; and the actual intensity corresponds to the reference intensity.

In some embodiments, a container contains a composition; the composition has an actual color; the actual color has an actual intensity; a label is attached to the container; the label comprises an image of a reference color to provide a consumer or other individual with a reference to an intended or desired color of the composition; the reference color has a reference intensity; the actual color corresponds to the reference color; and the actual intensity corresponds to the reference intensity. In some specific embodiments, a container contains a composition; the composition has an actual color; the actual color is purple; the actual color has an actual intensity; a label is attached to the container; the label comprises an image of a reference color to provide a consumer or other individual with a reference to an intended or desired color of the composition; the reference color is purple; the reference color has a reference intensity; and the actual intensity corresponds to the reference intensity. In some very specific embodiments, a container contains a composition; the composition has an actual color; the actual color is purple; the actual color has an actual shade; the actual shade is a shade of purple; the actual color has an actual intensity; a label is attached to the container; the label comprises an image of a reference color to provide a consumer or other individual with a reference to an intended or desired color of the composition; the reference color is purple; the reference color has a reference shade; the reference shade is the shade of purple; the reference color has a reference intensity; and the actual intensity corresponds to the reference intensity.

In some embodiments, a composition comprises water and an anionic cannabinoid molecule; and the anionic cannabinoid molecule is dissolved in the water at a concentration of 20 micrograms per liter to 2000 milligrams per liter. In some specific embodiments, an anionic cannabinoid molecule is dissolved in water at a concentration of 100 micrograms per liter to 1000 milligrams per liter. In some very specific embodiments, an anionic cannabinoid molecule is dissolved in water at a concentration of 200 micrograms per liter to 200 milligrams per liter.

In some embodiments, a composition comprises 50 micrograms to 500 milligrams of an anionic cannabinoid molecule. In some specific embodiments, a composition comprises 100 micrograms to 100 milligrams of an anionic cannabinoid molecule.

In some embodiments, a container contains 25 to 800 milliliters of a composition. In some specific embodiments, a container contains 50 to 300 milliliters of a composition. In some specific embodiments, a container contains 250 to 600 milliliters of a composition. In some specific embodiments, a container contains 400 to 800 milliliters of a composition.

In some embodiments, a composition has a pH, and the pH is 8.5 to 10.5.

In some embodiments, a composition is a liquid, and an anionic cannabinoid molecule is dissolved in the liquid.

In some embodiments, a composition is ice comprising an anionic cannabinoid molecule.

In some embodiments, a composition comprises ethanol at a concentration of 5 parts per billion to 500 parts per million by weight. In some specific embodiments, a composition comprises ethanol at a concentration of 5 parts per million to 500 parts per million by weight. In some very specific embodiments, a composition comprises ethanol at a concentration of 50 parts per million to 500 parts per million by weight.

In some embodiments, a composition comprises a concentration of molecular oxygen, and the concentration of molecular oxygen is less than 50 micromolar. In some specific embodiments, a composition lacks molecular oxygen at a concentration greater than 5 micromolar.

In some embodiments, a composition comprises a concentration of molecular nitrogen, and the concentration of molecular nitrogen is less than 100 micromolar. In some specific embodiments, a composition lacks molecular nitrogen at a concentration greater than 10 micromolar.

In some embodiments, a composition comprises hydroxide at a concentration of 1 micromolar to 100 micromolar.

In some embodiments, a sealed chamber is hermetically-sealed.

In some embodiments, a container is a glass bottle, a plastic bottle, or an aluminum can.

In some specific embodiments, a container contains 25 to 800 milliliters of a composition; the composition comprises water and an anionic cannabinoid molecule; the anionic cannabinoid molecule is dissolved in the water; the composition comprises 50 micrograms to 500 milligrams of the anionic cannabinoid molecule; the composition comprises the anionic cannabinoid molecule at a concentration of 100 micrograms per liter to 1000 milligrams per liter; the composition has a pH; the pH is 8.5 to 10.5; and the anionic cannabinoid molecule is 2-[(1R,6R)-6-isopropenyl-3-methylcyclohex-2-en-1-yl]-3-hydroxy-5-pentylphenolate.

In some very specific embodiments, a container contains 250 milliliters to 600 milliliters of a composition; the composition comprises water and an anionic cannabinoid molecule; the anionic cannabinoid molecule is dissolved in the water; the composition comprises 200 micrograms to 200 milligrams of the anionic cannabinoid molecule; the composition has a pH; the pH is 8.5 to 10.5; the anionic cannabinoid molecule is 2-[(1R,6R)-6-isopropenyl-3-methylcyclohex-2-en-1-yl]-3-hydroxy-5-pentylphenolate; the composition has a color; the color of the composition is purple; the container comprises a sealed chamber; the container contains the composition in the sealed chamber; and the sealed chamber is hermetically-sealed.

Various aspects of this patent document relate to a method to solubilize a cannabinoid in water.

In some embodiments, a method comprises providing a cannabinoid molecule, in which the cannabinoid molecule comprises an aromatic ring and a hydroxyl group, and the hydroxyl group is a substituent on the aromatic ring. In some specific embodiments, a cannabinoid molecule lacks a carboxyl group.

In some embodiments, a method comprises providing a Brønsted base.

In some embodiments, a method comprises providing water.

In some embodiments, a method comprises contacting a cannabinoid molecule with a Brønsted base to deprotonate a hydroxyl group of the cannabinoid molecule and to produce an anionic cannabinoid molecule.

In some embodiments, a method comprises dissolving an anionic cannabinoid molecule in water to produce a solution comprising the anionic cannabinoid molecule.

In some embodiments, a cannabinoid molecule is 2-[6-isopropenyl-3-methylcyclohex-2-en-1-yl]-5-pentylbenzene-1,3-diol. In some specific embodiments, a cannabinoid molecule is 2-[(1R,6R)-6-isopropenyl-3-methylcyclohex-2-en-1-yl]-5-pentylbenzene-1,3-diol ("cannabidiol").

In some embodiments, an anionic cannabinoid molecule is 2-[6-isopropenyl-3-methylcyclohex-2-en-1-yl]-3-hydroxy-5-pentylphenolate. In some specific embodiments, an anionic cannabinoid molecule is 2-[(1R,6R)-6-isopropenyl-3-methylcyclohex-2-en-1-yl]-3-hydroxy-5-pentylphenolate. In some very specific embodiments, a cannabinoid molecule is cannabidiol, and an anionic cannabinoid molecule is 2-[(1R,6R)-6-isopropenyl-3-methylcyclohex-2-en-1-yl]-3-hydroxy-5-pentylphenolate.

In some embodiments, a cannabinoid molecule is cannabidiol, and an anionic cannabinoid molecule is selected from 2-[(1R,6R)-6-isopropenyl-3-methylcyclohex-2-en-1-yl]-3-hydroxy-5-pentylphenolate; 2-[(1R,6R)-6-isopropenyl-3-methylcyclohex-3-en-1-yl]-3-hydroxy-5-pentylphenolate; 2-[(1R,6R)-6-isopropenyl-3-methylcyclohex-2-en-1-yl]-5-pentyl-1,4-benzoquinone-3-oxide; 3-[(1R,6R)-6-isopropenyl-3-methylcyclohex-2-en-1-yl]-6-pentyl-1,2-benzoquinone-4-oxide; 2-[(1R,6R)-6-isopropenyl-3-methylcyclohex-3-en-1-yl]-5-pentyl-1,4-benzoquinone-3-oxide; 3-[(1R,6R)-6-isopropenyl-3-methylcyclohex-3-en-1-yl]-6-pentyl-1,2-benzoquinone-4-oxide; (6aR,10aR)-6,6,9-trimethyl-3-pentyl-6a,7,8,10a-tetrahydro-6H-benzo[c]chromen-1-oxide; and (6aR,10aR)-6,6,9-trimethyl-3-pentyl-6a,7,10,10a-tetrahydro-6H-benzo[c]chromen-1-oxide.

In some embodiments, a Brønsted base is ethoxide or hydroxide.

In some embodiments, a cannabinoid molecule is dissolved in a solvent when the cannabinoid molecule is contacted with a Brønsted base.

In some embodiments, a Brønsted base is dissolved in a solvent when the Brønsted base is contacted with a cannabinoid molecule.

In some embodiments, a cannabinoid molecule and a Brønsted base are dissolved in a solvent when the cannabinoid molecule and the Brønsted base are contacted with each other.

In some embodiments, a solvent is ethanol.

In some embodiments, a solution comprising an anionic cannabinoid molecule comprises an ethanol concentration, and a method comprises adjusting the ethanol concentration of the solution to an ethanol concentration no greater than 0.05% by weight.

In some embodiments, a solvent has a dissolved oxygen concentration, and a method comprises reducing the dissolved oxygen concentration of the solvent prior to contacting a cannabinoid molecule with a Brønsted base.

In some embodiments, the water of a method has a dissolved oxygen concentration, and the method comprises reducing the dissolved oxygen concentration of the water prior to dissolving an anionic cannabinoid molecule in the water.

In some embodiments, the water of a method has a pH, and the pH is greater than 9.5.

In some embodiments, a solution comprising an anionic cannabinoid molecule has a pH, and a method comprises adjusting the pH to 8.5 to 10.5.

In some embodiments, a solution comprising an anionic cannabinoid molecule has a concentration of the anionic cannabinoid molecule, and a method comprises adjusting the concentration of the anionic cannabinoid molecule to a concentration of 20 micrograms per liter to 2000 milligrams per liter.

In some embodiments, a method results in a lipid phase in fluid communication with an aqueous phase that is a solution comprising an anionic cannabinoid molecule, and the method comprises separating the lipid phase from the solution.

In some embodiments, a method comprises freezing a solution comprising an anionic cannabinoid molecule to produce ice comprising the anionic cannabinoid molecule.

In some embodiments, a method comprises inserting a solution comprising an anionic cannabinoid molecule into a container and then hermetically-sealing the container.

In some embodiments, a method comprises inserting 25 milliliters to 800 milliliters of a solution comprising an anionic cannabinoid molecule into a container.

In some embodiments, a method comprises transferring ownership of a container containing a solution comprising an anionic cannabinoid molecule. In some embodiments, a method comprises receiving payment for transferring ownership of a container containing a solution comprising an anionic cannabinoid molecule.

In some embodiments, a method comprises transporting a container containing a solution comprising an anionic cannabinoid molecule such as in an intermodal freight container or in a refrigerated van or truck. In some specific embodiments, a method comprises transporting a container containing a solution comprising an anionic cannabinoid molecule, in which the container and the solution are refrigerated during the transporting. In some very specific embodiments, a method comprises freezing a solution comprising an anionic cannabinoid molecule to produce ice comprising the anionic cannabinoid molecule and then transporting the ice.

In some very specific embodiments, a cannabinoid molecule is cannabidiol; a method comprises contacting the cannabinoid molecule with a Brønsted base; the Brønsted base is dissolved in a solvent when the cannabinoid molecule is contacted with the Brønsted base; the solvent is ethanol; the Brønsted base is hydroxide or ethoxide; contacting the cannabinoid molecule with the Brønsted base produces an anionic cannabinoid molecule; the anionic cannabinoid molecule is 2-[(1R,6R)-6-isopropenyl-3-methylcyclohex-2-en-1-yl]-3-hydroxy-5-pentylphenolate; the method comprises dissolving the anionic cannabinoid molecule in water to produce a solution comprising the anionic cannabinoid molecule; the water has a pH; the pH of the water is greater than 9.5; the solution comprising the anionic cannabinoid molecule has a pH; either the pH of the solution is 8.5 to 10.5, or the method comprises adjusting the pH of the solution to 8.5 to 10.5; and the method comprises inserting the solution comprising the anionic cannabinoid molecule into a container and then hermetically-sealing the container.

Various aspects of this patent document relate to a method of administering a cannabinoid. In some embodiments, a method comprises providing a composition comprising an anionic cannabinoid molecule dissolved in water and administering the composition to a subject. In some specific embodiments, a subject is a human being.

In some embodiments, an anionic cannabinoid molecule is selected from 2-[(1R,6R)-6-isopropenyl-3-methylcyclohex-2-en-1-yl]-3-hydroxy-5-pentylphenolate; 2-[(1R,6R)-6-isopropenyl-3-methylcyclohex-3-en-1-yl]-3-hydroxy-5-pentylphenolate; 2-[(1R,6R)-6-isopropenyl-3-methylcyclohex-2-en-1-yl]-5-pentyl-1,4-benzoquinone-3-oxide; 3-[(1R,6R)-6-isopropenyl-3-methylcyclohex-2-en-1-yl]-6-pentyl-1,2-benzoquinone-4-oxide; 2-[(1R,6R)-6-isopropenyl-3-methylcyclohex-3-en-1-yl]-5-pentyl-1,4-benzoquinone-3-oxide; 3-[(1R,6R)-6-isopropenyl-3-methylcyclohex-3-en-1-yl]-6-pentyl-1,2-benzoquinone-4-oxide; (6aR,10aR)-6,6,9-trimethyl-3-pentyl-6a,7,8,10a-tetrahydro-6H-benzo[c]chromen-1-oxide; (6aR,10aR)-6,6,9-trimethyl-3-pentyl-6a,7,10,10a-tetrahydro-6H-benzo[c]chromen-1-oxide; 2-[(2E)-3,7-dimethylocta-2,6-dienyl]-3-hydroxy-5-pentylphenolate; 2-[(1R,6R)-6-isopropenyl-3-methylcyclohex-2-en-1-yl]-3-hydroxy-5-propylphenolate; 2-[(1R,6R)-6-isopropenyl-3-methylcyclohex-3-en-1-yl]-3-hydroxy-5-propylphenolate; 2-[(1R,6R)-6-isopropenyl-3-methylcyclohex-2-en-1-yl]-5-propyl-1,4-benzoquinone-3-oxide; 3-[(1R,6R)-6-isopropenyl-3-methylcyclohex-2-en-1-yl]-6-propyl-1,2-benzoquinone-4-oxide; 2-[(1R,6R)-6-isopropenyl-3-methylcyclohex-3-en-1-yl]-5-propyl-1,4-benzoquinone-3-oxide; 3-[(1R,6R)-6-isopropenyl-3-methylcyclohex-3-en-1-yl]-6-propyl-1,2-benzoquinone-4-oxide; (6aR,10aR)-6,6,9-trimethyl-3-propyl-6a,7,8,10a-tetrahydro-6H-benzo[c]chromen-1-oxide; (6aR,10aR)-6,6,9-trimethyl-3-propyl-6a,7,10,10a-tetrahydro-6H-benzo[c]chromen-1-oxide; and 2-[(2E)-3,7-dimethylocta-2,6-dienyl]-3-hydroxy-5-propylphenolate. In some specific embodiments, an anionic cannabinoid molecule is 2-[(1R,6R)-6-isopropenyl-3-methylcyclohex-3-en-1-yl]-3-hydroxy-5-pentylphenolate.

In some embodiments, administering a composition comprises oral, self-administration performed by a subject by drinking the composition.

In some embodiments, a method comprises providing a hermetically-sealed container containing a composition and unsealing the container to provide the composition. In some specific embodiments, a hermetically-sealed container contains 25 milliliters to 800 milliliters of a composition. In some specific embodiments, a hermetically-sealed container contains 50 micrograms to 500 milligrams of an anionic cannabinoid molecule. In some specific embodiments, a hermetically-sealed container is a glass bottle, plastic bottle, or aluminum can.

In some embodiments, a composition comprises an anionic cannabinoid molecule; the composition has an actual color; a container contains the composition; the container is physically associated with a label; the label comprises an image of a reference color; and a method comprises comparing the actual color with the reference color to either confirm the identity of the anionic cannabinoid molecule or confirm the approximate concentration of the anionic cannabinoid molecule in the composition.

In some embodiments, a composition has a color, and the color is purple.

In some embodiments, a composition has a color; a method comprises contacting the composition with a Brønsted acid prior to administering the composition; and contacting the composition with the Brønsted acid changes the color to either a different color or no color.

In some embodiments, a Brønsted acid is carbonic acid or citric acid. In some specific embodiments, contacting a composition with a Brønsted acid comprises contacting the composition with a carbonated liquid comprising carbonic acid. In some specific embodiments, contacting a composition with a Brønsted acid comprises contacting the composition with a juice from a *Citrus* fruit, in which the juice comprises citric acid. In some very specific embodiments, contacting a composition with a Brønsted acid comprises contacting the composition with a lemon, a lime, a juice of a lemon, or a juice of a lime.

In some embodiments, a composition has a pH, and the pH is 8.5 to 10.5.

In some embodiments, a composition comprises ethanol at a concentration of 5 parts per million to 500 parts per million by weight.

In some embodiments, a composition comprises a concentration of molecular oxygen, and the concentration of molecular oxygen is less than 50 micromolar. In some specific embodiments, a composition lacks molecular oxygen at a concentration greater than 5 micromolar.

In some embodiments, a composition comprises a concentration of molecular nitrogen, and the concentration of molecular nitrogen is less than 100 micromolar. In some specific embodiments, a composition lacks molecular nitrogen at a concentration greater than 10 micromolar.

In some specific embodiments, a method comprises: providing a hermetically-sealed container containing a composition comprising both water and an anionic cannabinoid molecule that is dissolved in the water; unsealing the hermetically-sealed container to provide the composition; and administering the composition to a subject, in which: the hermetically-sealed container is a glass bottle, plastic bottle, or aluminum can; the container contains 25 milliliters to 800 milliliters of the composition; the container contains 50 micrograms to 500 milligrams of the anionic cannabinoid molecule; the anionic cannabinoid molecule is 2-[(1R,6R)-6-isopropenyl-3-methylcyclohex-2-en-1-yl]-3-hydroxy-5-pentylphenolate; the composition has a pH; the pH of the composition is 8.5 to 10.5; the subject is a human being; and administering the composition is oral, self-administration performed by the subject by drinking the composition.

The words "comprising," "comprises," and "comprise" refer to open-ended sets. For example, a composition comprising water can also comprise ethanol.

The following exemplification section provides a framework to implement certain aspects of the disclosure, and the exemplification does not limit the scope of this patent document or any claim that matures from this patent document.

EXEMPLIFICATION

The experiments described in the following examples were initially performed to determine whether the conjugate base of cannabidiol-2-[(1R,6R)-6-isopropenyl-3-methylcyclohex-2-en-1-yl]-3-hydroxy-5-pentylphenolate-could be used to purify cannabidiol from tetrahydrocannabinol and other neutrally-charged lipids. It was contemplated that either (i) the production of 2-[(1R,6R)-6-isopropenyl-3-methylcyclohex-2-en-1-yl]-3-hydroxy-5-pentylphenolate in an aqueous phase would allow the mechanical separation of 2-[(1R,6R)-6-isopropenyl-3-methylcyclohex-2-en-1-yl]-3-hydroxy-5-pentylphenolate from a lipid phase containing tetrahydrocannabinol and other neutrally-charged lipids such as in a separatory funnel or such as by centrifugal partition chromatography, or (ii) the production of a 2-[(1R,6R)-6-isopropenyl-3-methylcyclohex-2-en-1-yl]-3-hydroxy-5-pentylphenolate salt would allow the separation of the 2-[(1R,6R)-6-isopropenyl-3-methylcyclohex-2-en-1-yl]-3-hydroxy-5-pentylphenolate salt from tetrahydrocannabinol and other volatile molecules by vaporizing the tetrahydrocannabinol and other volatile molecules. These experiments were not expected to result in useful compositions and methods, however, because the deprotonation of cannabidiol was thought to cause oxidation. The following experiments were nevertheless performed with the hope of identifying purification methods capable of outcompeting oxidation.

Examples 1-15 describe representative experiments that generated negative results.

Examples 16-18 describe successful proof-of-concept experiments.

Following the successful proof-of-concept experiments, the approximate $pK_a$ of cannabidiol in water was determined. Various $pK_a$'s have been reported and range from 9.13 to 9.64. If the $pK_a$ of cannabidiol were 9.13, which was the lowest previously-reported $pK_a$ for cannabidiol, then cannabidiol might be expected to lack stability in water at a pH of 9.5 because approximately 30% of the dissolved cannabidiol and 2-[(1R,6R)-6-isopropenyl-3-methylcyclohex-2-en-1-yl]-3-hydroxy-5-pentylphenolate would exist as cannabidiol, which might form a lipid phase. This lipid phase would be a thermodynamic sink if the lipid phase were to separate from the aqueous phase. Le Châtelier's principle could drive the conversion of 2-[(1R,6R)-6-isopropenyl-3-methylcyclohex-2-en-1-yl]-3-hydroxy-5-pentylphenolate into cannabidiol until the composition existed as an aqueous phase essentially devoid of 2-[(1R,6R)-6-isopropenyl-3-methylcyclohex-2-en-1-yl]-3-hydroxy-5-pentylphenolate and a lipid phase comprising cannabidiol. A greater $pK_a$, such as a $pK_a$ of 9.64, would magnify this detrimental effect. Examples 7 and 8 are consistent with the reported $pK_a$'s.

Example 19 unexpectedly suggested that the $pK_a$ of cannabidiol in water is substantially lower than all previously-reported values. This finding suggested for the first time that 2-[(1R,6R)-6-isopropenyl-3-methylcyclohex-2-en-1-yl]-3-hydroxy-5-pentylphenolate might be viable for inclusion in beverages.

Example 20 confirms that the $pK_a$ of cannabidiol in water is lower than all previously-reported $pK_a$ values.

Example 21 confirms that 2-[(1R,6R)-6-isopropenyl-3-methylcyclohex-2-en-1-yl]-3-hydroxy-5-pentylphenolate is stable in commercially-relevant embodiments.

Example 22 describes a molecular model of a dissolved state of 2-[(1R,6R)-6-isopropenyl-3-methylcyclohex-2-en-1-yl]-3-hydroxy-5-pentylphenolate in water, which might account for the unexpected $pK_a$ of cannabidiol in water.

Example 23 describes unexpectedly superior pharmacokinetic properties of 2-[(1R,6R)-6-isopropenyl-3-methylcyclohex-2-en-1-yl]-3-hydroxy-5-pentylphenolate dissolved in water relative to cannabidiol.

Example 24 provides third-party test results that confirm the stability and concentration of 2-[(1R,6R)-6-isopropenyl-3-methylcyclohex-2-en-1-yl]-3-hydroxy-5-pentylphenolate dissolved in water.

The findings described in this section reveal that 2-[(1R,6R)-6-isopropenyl-3-methylcyclohex-2-en-1-yl]-3-hydroxy-5-pentylphenolate is not only a viable intermediate for use in purification methods, but 2-[(1R,6R)-6-isopropenyl-3-methylcyclohex-2-en-1-yl]-3-hydroxy-5-pentylphenolate is also viable for inclusion in beverages. These findings are generally applicable to all known and yet-to-be-described cannabinoids that include an aromatic ring containing a hydroxyl substituent.

Example 1. Combining Crude Industrial Hemp Extract with Potassium Hydroxide Alone does not Produce 2-[(1R,6R)-6-isopropenyl-3-methylcyclohex-2-en-1-yl]-3-hydroxy-5-pentylphenolate 30 grams of potassium hydroxide was added to 155 grams of crude industrial hemp extract containing approximately 65% cannabidiol. The composition was stirred at 55° C. for 30 minutes. The potassium hydroxide remained present as white solid, and no color change indicative of a conversion from cannabidiol to 2-[(1R,6R)-6-isopropenyl-3-methylcyclohex-2-en-1-yl]-3-hydroxy-5-pentylphenolate was apparent. An aliquot of the composition was incubated overnight at 55° C., and no dissolution of the potassium hydroxide or color change was apparent.

Example 2. Combining Crude Industrial Hemp Extract with Potassium Hydroxide in an Approximate Equal-Volume of Water does not Produce an Appreciable Amount of 2-[(1R,6R)-6-isopropenyl-3-methylcyclohex-2-en-1-yl]-3-hydroxy-5-pentylphenolate 155 grams of distilled water was added to the mixture prepared in Example 1, and the composition was stirred at 55° C. for 30 minutes. The potassium hydroxide dissolved, and a purple sheen became apparent in the mixture, which suggests that at least some of the cannabidiol converted to 2-[(1R,6R)-6-isopropenyl-3-methylcyclohex-2-en-1-yl]-3-hydroxy-5-pentylphenolate. The mixture was incubated overnight at 55° C. to separate the aqueous phase from the lipid phase. The mixture was then cooled to solidify the lipid phase, and the aqueous phase and lipid phase were mechanically separated. Residual water was blotted from the lipid phase, and the lipid phase was further dehydrated in an oven. Visual examination of the lipid phase revealed a nominal purple layer on the surface of an ample brown core, which indicates that the experiment produced a minimal amount of 2-[(1R,6R)-6-isopropenyl-3-methylcyclohex-2-en-1-yl]-3-hydroxy-5-pentylphenolate that separated from the remaining crude industrial hemp extract.

Example 3. Combining Crude Industrial Hemp Extract with Potassium Hydroxide in Excess Water does not Produce an Appreciable Amount of 2-[(1R,6R)-6-isopropenyl-3-methylcyclohex-2-en-1-yl]-3-hydroxy-5-pentylphenolate 1.55 grams of crude industrial hemp extract comprising approximately 65% cannabidiol was suspended in 1.55 liters of distilled water to which 3 grams of potassium hydroxide was added. The suspension was vigorously stirred at 95° C. for 30 minutes in a closed flask. The pH of the suspension was determined to be only slightly alkaline, and so, a second aliquot of 3 grams of potassium hydroxide was added to the suspension. The suspension was vigorously stirred overnight at 55° C. The suspension was then allowed to separate with gentle stirring at 55° C., and the lipid phase floated to the top. The aqueous phase lacked a purple color indicative of a conversion from cannabidiol to 2-[(1R,6R)-6-isopropenyl-3-methyl cyclohex-2-en-1-yl]-3-hydroxy-5-pentylphenolate.

Example 4. Combining Cannabidiol Isolate with Potassium Hydroxide in Water Produces an Unknown Side Product 1 gram of cannabidiol isolate was vigorously mixed with 2.5 milliliters of water and excess potassium hydroxide at 95° C. The mixture initially formed a light purple lipid phase and a light purple aqueous phase. The purple lipid phase eventually formed crystals, and, after additional mixing at 95° C., the lipid phase formed a purple, semisolid mass. The semisolid mass was rinsed with water. 0.72 grams of the semisolid mass was dissolved in 1.5 milliliters of ethanol, and 0.17 grams of citric acid was added to the solution. The solution formed a reddish-brown liquid phase, which indicates that the experiment produced an unknown product.

Example 5. Combining Cannabidiol Isolate with Potassium Hydroxide in Glycerol Produces an Unknown Side Product 1 gram of potassium hydroxide was dissolved in 50 milliliters of glycerol with heating. 2.3 milliliters of the potassium hydroxide solution was added to 230 milligrams of cannabidiol isolate, and the mixture was heated with stirring. The cannabidiol did not completely dissolve in the glycerol, and so, 6.9 additional milliliters of the potassium hydroxide solution was added to the mixture. The cannabidiol then dissolved, and the solution became salmon-colored, which indicates that the experiment produced an unknown product.

Example 6. Combining Cannabidiol Isolate with Potassium Hydroxide in Ethanol Produces 2-[(1R, 6R)-6-isopropenyl-3-methylcyclohex-2-en-1-yl]-3-hydroxy-5-pentylphenolate 500 milligrams of cannabidiol isolate was dissolved in 5 milliliters of 350 millimolar potassium hydroxide in ethanol. The cannabidiol was deprotonated to form 2-[(1R,6R)-6-isopropenyl-3-methylcyclohex-2-en-1-yl]-3-hydroxy-5-pentylphenolate as evidenced by a strong purple color. 1 milliliter of the 2-[(1R,6R)-6-isopropenyl-3-methylcyclohex-2-en-1-yl]-3-hydroxy-5-pentylphenolate solution was added to a 500 milliliter bottle of FIJI® natural artesian water. The addition of the 2-[(1R,6R)-6-isopropenyl-3-methyl cyclohex-2-en-1-yl]-3-hydroxy-5-pentylphenolate to FIJI® water resulted in a color change from purple to colorless and resulted in an emulsion as evidenced by visual observation of the ouzo effect.

FIJI® water contains bicarbonate, which is a Brønsted acid that could re-protonate the 2-[(1R,6R)-6-isopropenyl-3-methylcyclohex-2-en-1-yl]-3-hydroxy-5-pentylphenolate. 1 milliliter of the 2-[(1R,6R)-6-isopropenyl-3-methylcyclohex-2-en-1-yl]-3-hydroxy-5-pentylphenolate solution was therefore also added to a 296 milliliter bottle of DASANI® purified water. The addition of the 2-[(1R,6R)-6-isopropenyl-3-methyl cyclohex-2-en-1-yl]-3-hydroxy-5-pentylphenolate to DASANI® water resulted in a color change from purple to colorless and resulted in an emulsion as evidenced by visual observation of the ouzo effect. The pH of the emulsion in DASANI® water was determined to be strongly alkaline.

These experiments suggest that 2-[(1R,6R)-6-isopropenyl-3-methylcyclohex-2-en-1-yl]-3-hydroxy-5-pentylphenolate in ethanol cannot be directly added to drinking water to produce a finished beverage.

Example 7. Attempt to Adjust the pH of 2-[(1R, 6R)-6-isopropenyl-3-methylcyclohex-2-en-1-yl]-3-hydroxy-5-pentylphenolate prepared from filtered industrial hemp extract 1.65 grams of carbon-filtered industrial hemp extract comprising approximately 65% cannabidiol was dissolved in 10 milliliters of 420 millimolar potassium hydroxide in ethanol to convert the cannabidiol into 2-[(1R,6R)-6-isopropenyl-3-methylcyclohex-2-en-1-yl]-3-hydroxy-5-pentylphenolate. The 2-[(1R,6R)-6-isopropenyl-3-methylcyclohex-2-en-1-yl]-3-hydroxy-5-pentylphenolate was then diluted with 90 milliliters of 100 millimolar sodium carbonate in water, which resulted in an emulsion as evidenced by visual observation of the ouzo effect. The pH of the emulsion was adjusted to 9.1 with 300 milliliters of 500 millimolar sodium bicarbonate, which resulted in the conversion of the 2-[(1R,6R)-6-isopropenyl-3-methylcyclohex-2-en-1-yl]-3-hydroxy-5-pentylphenolate back into cannabidiol as evidenced by a color change and separation of a lipid phase. This experiment suggested that the $pK_a$ of cannabidiol in water is greater than 9.1.

Example 8. Attempt to Adjust the pH of 2-[(1R, 6R)-6-isopropenyl-3-methylcyclohex-2-en-1-yl]-3-hydroxy-5-pentylphenolate Prepared from Cannabidiol Isolate 1 gram of cannabidiol isolate was dissolved in 10 milliliters of 380 millimolar potassium hydroxide in ethanol to convert the cannabidiol into 2-[(1R,6R)-6-isopropenyl-3-methyl cyclohex-2-en-1-yl]-3-hydroxy-5-pentylphenolate. The 2-[(1R,6R)-6-isopropenyl-3-methylcyclohex-2-en-1-yl]-3-hydroxy-5-pentylphenolate was then diluted with 90 milliliters of 100 millimolar sodium carbonate in water, which resulted in an emulsion as evidenced by visual observation of the ouzo effect. The pH of the emulsion was adjusted to 9.1 with 300 milliliters of 0.5 molar sodium bicarbonate, which resulted in the conversion of the 2-[(1R, 6R)-6-isopropenyl-3-methylcyclohex-2-en-1-yl]-3-hydroxy-5-pentylphenolate back into cannabidiol as evidenced by a color change and separation of a lipid phase. This experiment suggested that the $pK_a$ of cannabidiol in water is greater than 9.1.

Example 9. Attempt to Centrifuge an Emulsion Comprising 2-[(1R,6R)-6-isopropenyl-3-methylcyclohex-2-en-1-yl]-3-hydroxy-5-pentylphenolate 1.65 grams of carbon-filtered industrial hemp extract comprising approximately 65% cannabidiol was dissolved in 10 milliliters of 420 millimolar potassium hydroxide in ethanol to convert the cannabidiol into 2-[(1R,6R)-6-isopropenyl-3-methylcyclohex-2-en-1-yl]-3-hydroxy-5-pentylphenolate. The 2-[(1R,6R)-6-isopropenyl-3-methylcyclohex-2-en-1-yl]-3-hydroxy-5-pentylphenolate was then diluted with 80 milliliters of 110 millimolar sodium carbonate in water, which resulted in an emulsion as evidenced by visual observation of the ouzo effect. The emulsion was centrifuged in an unsuccessful attempt to phase-separate the emulsion.

Example 10. Attempt to Prepare 2-[(1R,6R)-6-isopropenyl-3-methylcyclohex-2-en-1-yl]-3-hydroxy-5-pentylphenolate from Crude Industrial Hemp Extract 33.3 grams of crude industrial hemp extract comprising approximately 65% cannabidiol was dissolved in 50 milliliters of 2.5 molar potassium hydroxide in ethanol to convert the cannabidiol into 2-[(1R,6R)-6-isopropenyl-3-methylcyclohex-2-en-1-yl]-3-hydroxy-5-pentylphenolate. The solution was diluted into 450 milliliters of 100 millimolar aqueous potassium hydroxide, and the solution rapidly formed an emulsion.

Example 11. Attempt to Prepare 2-[(1R,6R)-6-isopropenyl-3-methylcyclohex-2-en-1-yl]-3-hydroxy-5-pentylphenolate from Industrial Hemp Extract The experiment of Example 10 was repeated, but the 100 millimolar aqueous potassium hydroxide was added to the 50 milliliters of 2.5 molar potassium hydroxide in ethanol solution containing the 33.3 grams of 2-[(1R,6R)-6-isopropenyl-3-methylcyclohex-2-en-1-yl]-3-hydroxy-5-pentylphenolate (rather than adding the ethanol solution to the aqueous potassium hydroxide). This time, the solution did not appear to form an emulsion. The solution was added to 2000 milliliters of 1 molar sodium bicarbonate solution having a pH adjusted to 8.8 with potassium hydroxide, and the buffered solution formed an emulsion. This experiment suggests that it may be possible to dissolve 2-[(1R,6R)-6-isopropenyl-3-methyl cyclohex-2-en-1-yl]-3-hydroxy-5-pentylphenolate in water, but it might not be possible to buffer a solution of 2-[(1R,6R)-6-isopropenyl-3-methylcyclohex-2-en-1-yl]-3-hydroxy-5-pentylphenolate in water.

Example 12. Attempt to Prepare 2-[(1R,6R)-6-isopropenyl-3-methylcyclohex-2-en-1-yl]-3-hydroxy-5-pentylphenolate from Cannabidiol Isolate The experiment of Example 11 was repeated with cannabidiol isolate. 6.6 grams of cannabidiol isolate was dissolved in 10 milliliters of 2.5 molar potassium hydroxide in ethanol to convert the cannabidiol into 2-[(1R,6R)-6-isopropenyl-3-methylcyclohex-2-en-1-yl]-3-hydroxy-5-pentylphenolate. 90 milliliters of 100 millimolar aqueous potassium hydroxide was added to the 2-[(1R,6R)-6-isopropenyl-3-methylcyclohex-2-en-1-yl]-3-hydroxy-5-pentylphenolate in ethanol solution with stirring, and the solution formed an emulsion.

Example 13. Attempt to Prepare 2-[(1R,6R)-6-isopropenyl-3-methylcyclohex-2-en-1-yl]-3-hydroxy-5-pentylphenolate from Cannabidiol Isolate The experiment of Example 12 was repeated at a 1-to-5 dilution. 1.4 grams of cannabidiol isolate was dissolved in 10 milliliters of 0.5 molar potassium hydroxide in ethanol to convert the cannabidiol into 2-[(1R,6R)-6-isopropenyl-3-methylcyclohex-2-en-1-yl]-3-hydroxy-5-pentylphenolate. 90 milliliters of 100 millimolar aqueous sodium bicarbonate was added to the 2-[(1R,6R)-6-isopropenyl-3-methylcyclohex-2-en-1-yl]-3-hydroxy-5-pentylphenolate in ethanol solution with stirring, and the solution formed an emulsion.

Example 14. Attempt to Water-Solubilize 2-[(1R,6R)-6-isopropenyl-3-methylcyclohex-2-en-1-yl]-3-hydroxy-5-pentylphenolate from a Potassium Salt 1.4 grams of pure cannabidiol was dissolved in 10 milliliters of 0.5 molar potassium hydroxide in ethanol to convert the cannabidiol into 2-[(1R,6R)-6-isopropenyl-3-methylcyclohex-2-en-1-yl]-3-hydroxy-5-pentylphenolate. A potassium salt of 2-[(1R,6R)-6-isopropenyl-3-methylcyclohex-2-en-1-yl]-3-hydroxy-5-pentylphenolate was formed by drying the ethanol solution under vacuum overnight. 90 milliliters of 100 millimolar aqueous sodium carbonate was added to the potassium salt of 2-[(1R,6R)-6-isopropenyl-3-methylcyclohex-2-en-1-yl]-3-hydroxy-5-pentylphenolate. A portion of the potassium salt of 2-[(1R,6R)-6-isopropenyl-3-methylcyclohex-2-en-1-yl]-3-hydroxy-5-pentylphenolate dissolved, but the majority of the salt remained in the solid phase. This experiment suggests that it might not be possible to dissolve an appreciable amount of 2-[(1R,6R)-6-isopropenyl-3-methylcyclohex-2-en-1-yl]-3-hydroxy-5-pentylphenolate in water.

Example 15. Removal of Ethanol from 2-[(1R,6R)-6-isopropenyl-3-methylcyclohex-2-en-1-yl]-3-hydroxy-5-pentylphenolate in a Vacuum Oven Produces an Unknown Side Product 372 grams of crude industrial hemp extract containing approximately 65% cannabidiol was dissolved in ethanol at a weight ratio of 1:2 crude to ethanol. 43.2 grams of potassium hydroxide was slowly added to the hemp extract in ethanol, and the solution was stirred while heating at 55° C. The solution was then placed in an oven under vacuum and slowly ramped to a temperature of 157° C. over the course of approximately 1 hour, at which time heating was discontinued. The solution was then left in the oven under vacuum overnight.

The product produced by ethanol removal in an oven under vacuum was purple with a taffy-like consistency indicative of polymer formation. The product lacked appreciable solubility in water. This experiment suggests that 2-[(1R,6R)-6-isopropenyl-3-methylcyclohex-2-en-1-yl]-3-hydroxy-5-pentylphenolate is unstable at high temperatures.

Example 16. Preparation of 2-[(1R,6R)-6-isopropenyl-3-methylcyclohex-2-en-1-yl]-3-hydroxy-5-pentylphenolate Dissolved in Water This example describes the first successful attempt to solubilize 2-[(1R,6R)-6-isopropenyl-3-methylcyclohex-2-en-1-yl]-3-hydroxy-5-pentylphenolate in water. 0.5 grams of cannabidiol was dissolved in 3.3 milliliters of 0.5 molar potassium hydroxide in ethanol to produce 2-[(1R,6R)-6-isopropenyl-3-methylcyclohex-2-en-1-yl]-3-hydroxy-5-pentylphenolate. The conversion of cannabidiol to 2-[(1R,6R)-6-isopropenyl-3-methyl cyclohex-2-en-1-yl]-3-hydroxy-5-pentylphenolate was readily confirmed by color because cannabidiol lacks discernable color and 2-[(1R,6R)-6-isopropenyl-3-methylcyclohex-2-en-1-yl]-3-hydroxy-5-pentylphenolate has a deep purple color.

The 2-[(1R,6R)-6-isopropenyl-3-methylcyclohex-2-en-1-yl]-3-hydroxy-5-pentylphenolate was diluted with 26.7 milliliters of 100 millimolar sodium carbonate in water. The mixture produced an emulsion as evidenced by visual observation of the ouzo effect. Centrifugation was attempted to phase-separate the emulsion, and phase separation was surprisingly successful (compare with Example 9). This example differs from Example 9 in that this example used cannabidiol isolate, which had a purity greater than 95% by weight, relative to the industrial hemp extract of Example 9, which had a purity of approximately 65% by weight. The supernatant was divided into three aliquots of 10 milliliters each for use in other experiments.

Example 17. Preparation of Salts Comprising 2-[(1R,6R)-6-isopropenyl-3-methylcyclohex-2-en-1-yl]-3-hydroxy-5-pentylphenolate This example describes a successful attempt to produce a salt of 2-[(1R,6R)-6-isopropenyl-3-methylcyclohex-2-en-1-yl]-3-hydroxy-5-pentylphenolate that readily dissolves in water.

A first aliquot from Example 16 was lyophilized to produce salts including a potassium 2-[(1R,6R)-6-isopropenyl-3-methylcyclohex-2-en-1-yl]-3-hydroxy-5-pentylphenolate salt and a sodium 2-[(1R,6R)-6-isopropenyl-3-methylcyclohex-2-en-1-yl]-3-hydroxy-5-pentylphenolate salt. The lyophilized salt was added to distilled water, and a portion of the salt immediately dissolved in the water as evidenced by a color change from transparent colorless to transparent purple. The water was centrifuged to remove undissolved salt and to produce an aqueous solution of 2-[(1R,6R)-6-isopropenyl-3-methylcyclohex-2-en-1-yl]-3-hydroxy-5-pentylphenolate concentrate for inclusion in beverages.

Example 18. Reconstituting Cannabidiol from 2-[(1R,6R)-6-isopropenyl-3-methylcyclohex-2-en-1-yl]-3-hydroxy-5-pentylphenolate 0.1 milliliters of 5 molar citric acid was added to an aliquot from Example 16 to reconstitute cannabidiol from 2-[(1R,6R)-6-isopropenyl-3-methylcyclohex-2-en-1-yl]-3-hydroxy-5-pentylphenolate. The reconstitution of cannabidiol was confirmed by color.

Example 19. Determining that the $pK_a$ of Cannabidiol in Water is Lower than Previously Reported 1 gram of cannabidiol was dissolved in 6.6 milliliters of 0.5 molar potassium hydroxide in ethanol to produce 2-[(1R,6R)-6-isopropenyl-3-methylcyclohex-2-en-1-yl]-3-hydroxy-5-pentylphenolate. The solution was then diluted with 100 millimolar sodium carbonate in water to a final volume of 50 milliliters to produce a solution comprising 2-[(1R,6R)-6-isopropenyl-3-methylcyclohex-2-en-1-yl]-3-hydroxy-5-pentylphenolate at approximately 20-grams-per-liter. 0.5 milliliters of the 2-[(1R,6R)-6-isopropenyl-3-methylcyclohex-2-en-1-yl]-3-hydroxy-5-pentylphenolate solution was added to each of 25 test tubes containing 9.5 milliliters of 100 millimolar (0.1 M) carbonate/bicarbonate ($CO_3^{2-}/HCO_3^-$) buffer according to Table 1. Each test tube contained approximately 10 milligrams of 2-[(1R,6R)-6-isopropenyl-3-methylcyclohex-2-en-1-yl]-3-hydroxy-5-pentylphenolate at a concentration of approximately 1 gram-per-liter. pH's were confirmed by multiple different measurements.

TABLE 1

Aqueous compositions comprising 2-[(1R,6R)-6-isopropenyl-3-methylcyclohex-2-en-1-yl]-3-hydroxy-5-pentylphenolate at variable pH

| Sample | pH | 0.1M $CO_3^{2-}$ * | 0.1M $HCO_3^-$ |
|---|---|---|---|
| 1 | 9.1 | 0.06 mL | 8.94 mL |
| 2 | 9.2 | 0.20 mL | 8.80 mL |
| 3 | 9.3 | 0.36 mL | 8.64 mL |
| 4 | 9.4 | 0.56 mL | 8.44 mL |
| 5 | 9.5 | 0.80 mL | 8.20 mL |
| 6 | 9.6 | 1.08 mL | 7.92 mL |
| 7 | 9.7 | 1.41 mL | 7.59 mL |
| 8 | 9.8 | 1.78 mL | 7.22 mL |
| 9 | 9.9 | 2.21 mL | 6.79 mL |
| 10 | 10.0 | 2.67 mL | 6.33 mL |
| 11-13 | 10.3 | 4.25 mL | 4.75 mL |
| 14-16 | 10.4 | 4.79 mL | 4.21 mL |
| 17-19 | 10.5 | 5.32 mL | 3.68 mL |
| 20-22 | 11.0 | 7.42 mL | 1.58 mL |
| 23-25 | 11.5 | 8.44 mL | 0.56 mL |

*The amount of $CO_3^{2-}$ in Table 1 does not include the approximately 0.5 milliliters of 100 millimolar sodium carbonate that was added with the 0.5 milliliters of 20 gram-per-liter solution of 2-[(1R,6R)-6-isopropenyl-3-methylcyclohex-2-en-1-yl]-3-hydroxy-5-pentylphenolate.

It was expected that 2-[(1R,6R)-6-isopropenyl-3-methylcyclohex-2-en-1-yl]-3-hydroxy-5-pentylphenolate would reform cannabidiol at pH's below a threshold pH as evidenced by an expected color change from purple (indicative of 2-[(1R,6R)-6-isopropenyl-3-methylcyclohex-2-en-1-yl]-3-hydroxy-5-pentylphenolate) to colorless (indicative of cannabidiol). No color change occurred at pH's of 9.1 and above. This finding suggested for the first time that the $pK_a$ of cannabidiol is less than 9.1 in dilute aqueous solutions and that 2-[(1R,6R)-6-isopropenyl-3-methylcyclohex-2-en-1-yl]-3-hydroxy-5-pentylphenolate is a viable ingredient for inclusion in beverages.

Example 20. Determining the Approximate $pK_a$ of Cannabidiol

This example confirms that 2-[(1R,6R)-6-isopropenyl-3-methylcyclohex-2-en-1-yl]-3-hydroxy-5-pentylphenolate is viable for inclusion in beverages formulated for human consumption. 0.5 milliliters of the 20 gram-per-liter solution of 2-[(1R,6R)-6-isopropenyl-3-methylcyclohex-2-en-1-yl]-3-hydroxy-5-pentylphenolate described in Example 19 was diluted with 9.5 milliliters of distilled water comprising varying concentrations of sodium bicarbonate, and color was monitored as shown in Table 2. pH's were confirmed by multiple different measurements.

TABLE 2

Samples used to determine an approximate $pK_a$ for cannabidiol

| Sample | pH | $NaHCO_3$ concentration in millimolar | color |
|---|---|---|---|
| 26 | 8.0 | 1000 | faint purple |
| 27 | 8.3 | 500 | light purple |
| 28 | 8.6 | 250 | Purple |
| 29 | 8.9 | 125 | Purple |
| 30 | 9.2 | 62 | Purple |

A color change was visually apparent at a pH of 8.0, and a subtle color change was visually apparent at pH of 8.3. These findings suggest that the $pK_a$ of cannabidiol in dilute aqueous solution is between 8.0 and 8.5. This result was surprising given that previously-reported $pK_a$'s for cannabidiol range from 9.13 to 9.64 and because the chemically-related molecule resorcinol has a $pK_a$ of 9.15. Further, even though sample 26, which had a pH of 8.0, displayed a color change indicative of conversion from 2-[(1R,6R)-6-isopropenyl-3-methylcyclohex-2-en-1-yl]-3-hydroxy-5-pentylphenolate to cannabidiol, no lipid phase formed, which suggests that the interconversion between 2-[(1R,6R)-6-isopropenyl-3-methylcyclohex-2-en-1-yl]-3-hydroxy-5-pentylphenolate and cannabidiol in aqueous solution can kinetically trap cannabidiol in the aqueous phase and inhibit the production of a lipid phase. These findings suggest that 2-[(1R,6R)-6-isopropenyl-3-methylcyclohex-2-en-1-yl]-3-hydroxy-5-pentylphenolate, the conjugate base of cannabidiol, is suitable for use in beverages for human consumption.

Example 21. Confirming the Commercial Viability of Beverages Comprising 2-[(1R,6R)-6-isopropenyl-3-methylcyclohex-2-en-1-yl]-3-hydroxy-5-pentylphenolate 20 milliliters of water was removed from a 1 liter bottle of ESSENTIA® OVERACHIEVING H₂O®. ESSENTIA® OVERACHIEVING H₂O® contains purified water, sodium bicarbonate, dipotassium phosphate, magnesium sulfate, and calcium chloride, and its pH was determined to be about 9.5. The 20 milliliters of removed water was replaced with 20 milliliters of the 20 gram-per-liter solution of 2-[(1R,6R)-6-isopropenyl-3-methylcyclohex-2-en-1-yl]-3-hydroxy-5-pentylphenolate, which is described in Example 19, and the bottle was sealed using the screw-cap top of the bottle to produce a sealed container containing approximately 400 milligrams of 2-[(1R,6R)-6-isopropenyl-3-methylcyclohex-2-en-1-yl]-3-hydroxy-5-pentylphenolate. The pH of the liquid was measured and determined to be about 10. The liquid was purple and transparent.

5 milliliters of water was removed from a 500 milliliter bottle of DASANI® purified water. DANSANI® purified water contains purified water, magnesium sulfate, potassium chloride, and sodium chloride, and its pH was determined to be about 7.0. The 5 milliliters of removed water was replaced with 5 milliliters of the 20 gram-per-liter solution of 2-[(1R,6R)-6-isopropenyl-3-methylcyclohex-2-en-1-yl]-3-hydroxy-5-pentylphenolate, which is described in Example 19, and the bottle was sealed using the screw-cap top of the bottle to produce a sealed container containing approximately 100 milligrams of 2-[(1R,6R)-6-isopropenyl-3-methylcyclohex-2-en-1-yl]-3-hydroxy-5-pentylphenolate. The pH of the liquid was measured and determined to be about 9.5. The liquid was transparent and purple.

0.5 milliliters of water was removed from a 500 milliliter bottle of DASANI® purified water. The 0.5 milliliters of removed water was replaced with 0.5 milliliters of the 20 gram-per-liter solution of 2-[(1R,6R)-6-isopropenyl-3-methylcyclohex-2-en-1-yl]-3-hydroxy-5-pentylphenolate, which is described in Example 19, and the bottle was sealed using the screw-cap top of the bottle to produce a sealed container containing approximately 10 milligrams of 2-[(1R,6R)-6-isopropenyl-3-methylcyclohex-2-en-1-yl]-3-hydroxy-5-pentylphenolate. The pH of the liquid was measured and determined to be about 8.5. The liquid was transparent and lacked discernable color.

The preceding experiments confirm that 2-[(1R,6R)-6-isopropenyl-3-methylcyclohex-2-en-1-yl]-3-hydroxy-5-pentylphenolate is suitable for use in commercially-relevant beverages.

Example 22. Molecular Model of 2-[(1R,6R)-6-isopropenyl-3-methylcyclohex-2-en-1-yl]-3-hydroxy-5-pentylphenolate 2-[(1R,6R)-6-isopropenyl-3-methylcyclohex-2-en-1-yl]-3-hydroxy-5-pentylphenolate was modeled in three dimensions to identify molecular features that might result in a lower $pK_a$ than resorcinol and other related molecules. Two water molecules are capable of hydrogen bonding with the 1-oxide oxygen of 2-[(1R,6R)-6-isopropenyl-3-methylcyclohex-2-en-1-yl]-3-hydroxy-5-pentylphenolate and the pi cloud of its 4-carbon, which carries a partial negative charge from its keto-resonance structures (the FIGURE, fourth and second grey water molecules from the left, respectively). These two water molecules can hydrogen-bond with a third water molecule (the FIGURE, third grey water molecule from the left) with bond lengths and bond geometries that are similar to those found in ice, which indicates a strong likelihood of stable coordination of water by 2-[(1R,6R)-6-isopropenyl-3-methylcyclohex-2-en-1-yl]-3-hydroxy-5-pentylphenolate. The oxygen atom of the third water molecule would be about 3.0 to 3.5 angstroms away from the 2-carbon of the cyclohexenyl group, and the 2-proton would be nearly in-line with the line connecting the water oxygen and the 2-carbon, which suggests a favorable interaction similar to a hydrogen bond (not shown). A fourth water molecule (the FIGURE, first grey water molecule from the left) can connect the three other waters to the 3-hydroxyl of 2-[(1R,6R)-6-isopropenyl-3-methylcyclohex-2-en-1-yl]-3-hydroxy-5-pentylphenolate by forming two additional hydrogen bonds.

The FIGURE shows that four coordinated water molecules can directly connect the 1-oxide of 2-[(1R,6R)-6-isopropenyl-3-methylcyclohex-2-en-1-yl]-3-hydroxy-5-pentylphenolate with its 3-hydroxyl through a chain of hydrogen bonds. In this configuration, the protonation of the 1-oxide oxygen is disfavored, and protonation could nevertheless result in the deprotonation of the 3-hydroxyl group, thereby regenerating 2-[(1R,6R)-6-isopropenyl-3-methylcyclohex-2-en-1-yl]-3-hydroxy-5-pentylphenolate. Specifically, the protonation of the 1-oxide oxygen could deprotonate a bound water (the FIGURE, fourth grey water molecule from the left), which could deprotonate a second bound water (the FIGURE, third grey water molecule from the left), which could deprotonate a third bound water (the FIGURE, second grey water molecule from the left), which could deprotonate a fourth bound water (the FIGURE, first grey water molecule from the left), which could deprotonate the 3-hydroxyl group, to regenerate 2-[(1R,6R)-6-isopropenyl-3-methylcyclohex-2-en-1-yl]-3-hydroxy-5-pentylphenolate. Each of these four, bound waters displays near-ideal bond lengths and bond geometries in the model depicted in the FIGURE, which suggests that this configuration and similar configurations contribute to the unexpected, surprising stability of 2-[(1R,6R)-6-isopropenyl-3-methylcyclohex-2-en-1-yl]-3-hydroxy-5-pentylphenolate in water at pH's ranging from 8.5 to 10.5.

Example 23. Qualitative Assessment of the Pharmacokinetics of 2-[(1R,6R)-6-isopropenyl-3-methylcyclohex-2-en-1-yl]-3-hydroxy-5-pentylphenolate in Humans Approximately 60 milligrams of 2-[(1R,6R)-6-isopropenyl-3-methylcyclohex-2-en-1-yl]-3-hydroxy-5-pentylphenolate prepared from crude industrial hemp extract was dissolved in water as described in Example 16, buffered to a pH of 9.1, and added to a 296 milliliter bottle of DASANI® purified water. The resultant solution was transparent, had a purple color, and had an approximate concentration of 200 milligrams per liter. A healthy, consenting adult self-administered the entire bottle of 60 milligrams of 2-[(1R,6R)-6-isopropenyl-3-methylcyclohex-2-en-1-yl]-3- hydroxy-5-pentylphenolate in water orally over 5 to 10 minutes. The individual reported experiencing the rapid onset of a perceptible psychoactive effect within minutes of ingestion followed by a marked perceptible psychoactive effect approximately 30 minutes following ingestion. The individual described the psychoactive effect as a pleasant sensation accompanied by both an enhanced ability to focus and elevated alertness.

Approximately 30 milligrams of 2-[(1R,6R)-6-isopropenyl-3-methylcyclohex-2-en-1-yl]-3-hydroxy-5-pentylphenolate prepared from crude industrial hemp extract was dissolved in water, buffered to a pH of 9.1, and added to each of four 296 milliliter bottles of DASANI® purified water. The resultant solutions were transparent, had a purple color, and approximate concentrations of 100 milligrams per liter. Four healthy, consenting adults orally self-administered varying amounts of the four solutions over 5 to 10 minutes. Three of the four individuals reported experiencing a rapid onset of a perceptible psychoactive effect similar to the psychoactive effect described above within minutes of ingestion.

This example is consistent with the hypothesis that 2-[(1R,6R)-6-isopropenyl-3-methylcyclohex-2-en-1-yl]-3-hydroxy-5-pentylphenolate is rapidly converted into cannabidiol upon contacting the oral mucosa and that at least some of the cannabidiol adheres to the epithelial lining of the buccal cavity, and possibly the esophagus, through which the cannabidiol is rapidly absorbed. Any 2-[(1R,6R)-6-isopropenyl-3-methylcyclohex-2-en-1-yl]-3-hydroxy-5-pentylphenolate that reaches the stomach would be quickly converted into cannabidiol by hydronium ion, and the cannabidiol would similarly favor adherence to the epithelial lining of the stomach followed by rapid absorption. This digestive mechanism is inapposite to the digestion of cannabidiol in vegetable oil carriers, in which the cannabidiol would be expected to remain sequestered within a lipid phase that would be expected to float on the surface of the gastric juice until gastric emptying, after which the lipases of the small intestine could hydrolyze the lipids for absorption of the cannabidiol through the epithelial lining of the small intestine.

2-[(1R,6R)-6-isopropenyl-3-methylcyclohex-2-en-1-yl]-3-hydroxy-5-pentylphenolate dissolved in water has multiple pharmacokinetic advantages over cannabidiol dissolved in vegetable oils, including (i) increased effective surface area, (ii) absorption through the epithelial lining of the mouth, which bypasses first-pass metabolism and allows rapid pharmacological effects, (iii) absorption in the stomach, which allows rapid pharmacological effects relative to absorption in the small intestine, and (iv) avoidance of digestive enzymes, including the digestive enzymes of the small intestine. 2-[(1R,6R)-6-isopropenyl-3-methylcyclohex-2-en-1-yl]-3-hydroxy-5-pentylphenolate dissolved in water delivers a more reproducible bolus of cannabidiol relative to cannabidiol dissolved in a vegetable oil carrier for the reasons described above. 2-[(1R,6R)-6-isopropenyl-3-methylcyclohex-2-en-1-yl]-3-hydroxy-5-pentylphenolate dissolved in water delivers a larger effective amount of cannabidiol relative to the same amount of cannabidiol dissolved in a vegetable oil carrier for the reasons described above.

Example 24. Confirmation of 2-[(1R,6R)-6-isopropenyl-3-methylcyclohex-2-en-1-yl]-3-hydroxy-5-pentylphenolate Dissolved in Water by an Accredited, Third-Party Laboratory Pure cannabidiol was deprotonated and dissolved in water using a strategy similar to those described in Examples 16 and 19. Acetic acid was then added to 100 milliliters of the water, dropwise, until the purple color disappeared to reform cannabidiol. Reprotonated cannabidiol was extracted from the water using 4 milliliters of olive oil. Two 1 milliliter samples of the olive oil were sent to Botanacor Laboratories (Boulder, Colo.) for cannabinoid profile analysis using an Agilent Technologies (Santa Clara, Calif.) High Performance Liquid Chromatography instrument with a diode array detector. Botanacor Laboratories is ISO/IEC 17025 accredited for cannabinoid potency determination. Botanacor Laboratories determined that the two olive oil samples contained 0.18% and 0.21% cannabidiol by weight and did not detect any other cannabinoid in the samples. This experiment suggests that 2-[(1R,6R)-6-isopropenyl-3-methylcyclohex-2-en-1-yl]-3-hydroxy-5-pentylphenolate was dissolved in water at a concentration of about 78 milligrams per liter.

What is claimed is:

1. A method to solubilize a cannabinoid in water, comprising:
    providing a cannabinoid molecule, the cannabinoid molecule is cannabidiol and comprises an aromatic ring and a hydroxyl group, and the hydroxyl group is a substituent on the aromatic ring;
    providing a Brønsted base and ethanol;
    providing water;
contacting the cannabinoid molecule with the Brønsted base and the ethanol to deprotonate the hydroxyl group and to produce an anionic cannabinoid molecule; and
    dissolving the anionic cannabinoid molecule in the water to produce a solution comprising the anionic cannabinoid molecule;
    the solution comprising the anionic cannabinoid molecule has a pH of at least 8.5; and the anionic cannabinoid molecule is selected from the group consisting of:
2-[(1R,6R)-6-isopropenyl-3-methylcyclohex-2-en-1-yl]-3-hydroxy-5-pentylphenolate; 2-[(1R,6R)-6-isopropenyl-3-methylcyclohex-3-en-1-yl]-3-hydroxy-5-pentylphenolate;
2-[(1R,6R)-6-isopropenyl-3-methylcyclohex-2-en-1-yl]-5-pentyl-1,4-benzoquinone-3-oxide;
3-[(1R,6R)-6-isopropenyl-3-methylcyclohex-2-en-1-yl]-6-pentyl-1,2-benzoquinone-4-oxide;
2-[(1R,6R)-6-isopropenyl-3-methylcyclohex-3-en-1-yl]-5-pentyl-1,4-benzoquinone-3-oxide;
3-[(1R,6R)-6-isopropenyl-3-methylcyclohex-3-en-1-yl]-6-pentyl-1,2-benzoquinone-4-oxide; and
(6aR,10aR)-6,6,9-trimethyl-3-pentyl-6a,7,10,10a-tetrahydro-6H-benzo[c]chromen-1-oxide.

2. The method of claim 1, in which the cannabinoid molecule is cannabidiol, and the anionic cannabinoid molecule is 2-[(1R,6R)-6-isopropenyl-3-methylcyclohex-2-en-1-yl]-3-hydroxy-5-pentylphenolate.

3. The method of claim 1, in which the Brønsted base is ethoxide or hydroxide.

4. The method of claim 1, which either (i) the cannabinoid molecule, (ii) the Brønsted base, or (iii) both the cannabinoid molecule and the Brønsted base are dissolved in a solvent when the cannabinoid molecule and the Brønsted base are contacted with each other.

5. The method of claim 4, in which the solvent is ethanol.

6. The method of claim 5, which the solution has an ethanol concentration, and the method comprises adjusting the ethanol concentration of the solution to an ethanol concentration no greater than 0.05% by weight.

7. The method of claim 4, in which the solvent has a dissolved oxygen concentration, and the method comprises reducing the dissolved oxygen concentration of the solvent prior to contacting the cannabinoid molecule with the Brønsted base.

8. The method of claim 1, which the water has a dissolved oxygen concentration, and the method comprises reducing the dissolved oxygen concentration of the water prior to dissolving the anionic cannabinoid molecule in the water.

9. The method of claim 1, in which the water has a pH, and the pH is greater than 9.5.

10. The method of claim 1, in which the solution comprising the anionic cannabinoid molecule has a pH, and the method comprises adjusting the pH to 8.5 to 10.5.

11. The method of claim 1, comprising adjusting a concentration of the anionic cannabinoid molecule in the solution to a concentration of 20 micrograms per liter to 2000 milligrams per liter.

12. The method of claim 1, in which the method results in a lipid phase in fluid communication with the solution comprising the anionic cannabinoid molecule, and the method comprises separating the lipid phase from the solution.

13. The method of claim 1, comprising inserting the solution comprising the anionic cannabinoid molecule into a container and then hermetically-sealing the container.

14. The method of claim 13, comprising inserting 25 milliliters to 800 milliliters of the solution into the container.

15. The method of claim 13, comprising transferring ownership of the container and receiving payment for transferring ownership of the container.

16. The method of claim 1, in which:
the cannabinoid molecule is cannabidiol;
the anionic cannabinoid molecule is 2-[(1R,6R)-6-isopropenyl-3-methylcyclohex-2-en-1-yl]-3-hydroxy-5-pentylphenolate;
the Brønsted base is dissolved in a solvent when the cannabinoid molecule and the Brønsted base are contacted with each other;
the solvent is ethanol;
the Brønsted base is hydroxide or ethoxide;
the water has a pH;
the pH of the water is greater than 9.5;
the solution comprising the anionic cannabinoid molecule has a pH;
either the pH of the solution is 8.5 to 10.5, or the method comprises adjusting the pH of the solution to 8.5 to 10.5; and
the method comprises inserting the solution comprising the anionic cannabinoid molecule into a container and then hermetically-sealing the container.

* * * * *